United States Patent
Tee, Jr. et al.

(10) Patent No.: US 10,653,571 B2
(45) Date of Patent: May 19, 2020

(54) ARTICLE COMPRISING ODOR CONTROL COMPOSITION

(71) Applicant: The Procter & Gamble Company, Cincinnati, OH (US)

(72) Inventors: Johannson Jimmy Tee, Jr., Mason, OH (US); Kristin Hofmann Miller, Springboro, OH (US); William Winfield Cheeseman, Springboro, OH (US); Ebrahim Rezai, Mason, OH (US); Marc Jennewein, Taunusstein (DE); Walter van de Klugt, Mechernich (DE); Zaiyou Liu, West Chester, OH (US); Melissa Jane Wene, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 617 days.

(21) Appl. No.: 15/372,492

(22) Filed: Dec. 8, 2016

(65) Prior Publication Data

US 2017/0165134 A1    Jun. 15, 2017

Related U.S. Application Data

(60) Provisional application No. 62/265,438, filed on Dec. 10, 2015.

(51) Int. Cl.
*A61F 13/84*    (2006.01)
*A61F 13/537*   (2006.01)
(Continued)

(52) U.S. Cl.
CPC ........ *A61F 13/8405* (2013.01); *A61F 13/539* (2013.01); *A61F 13/53747* (2013.01); *A61F 2013/5315* (2013.01); *A61F 2013/53472* (2013.01); *A61F 2013/842* (2013.01); *A61F 2013/8408* (2013.01); *A61F 2013/8423* (2013.01); *A61F 2013/8429* (2013.01)

(58) Field of Classification Search
CPC .......... A61F 13/8405; A61F 2013/8408; A61F 2013/842; A61F 2013/5315; A61F 2013/53472; A61F 13/53747; A61F 13/539

See application file for complete search history.

(56) References Cited

U.S. PATENT DOCUMENTS

| | | | |
|---|---|---|---|
| 3,340,875 | A | 9/1967 | Dudley et al. |
| 3,344,789 | A | 10/1967 | Warren et al. |

(Continued)

FOREIGN PATENT DOCUMENTS

| | | |
|---|---|---|
| AU | 2012205144 A1 | 8/2012 |
| BE | 815446 A1 | 9/1974 |

(Continued)

OTHER PUBLICATIONS

PCT International Search Report, PCT/US2016/065603, dated Feb. 23, 2017, 14 pages.

*Primary Examiner* — Susan S Su
(74) *Attorney, Agent, or Firm* — Daniel S. Albrecht; Kathleen Y. Carter

(57) ABSTRACT

Absorbent articles comprising odor control compositions that are not visible from the outside of the article due to placement on or next to the absorbent core wrap.

20 Claims, 9 Drawing Sheets

(51) Int. Cl.
*A61F 13/539* (2006.01)
*A61F 13/531* (2006.01)
*A61F 13/534* (2006.01)

(56) References Cited

U.S. PATENT DOCUMENTS

| | | | |
|---|---|---|---|
| 3,856,014 | A | 12/1974 | Yamauchi |
| 3,860,003 | A | 1/1975 | Buell |
| 3,939,838 | A | 2/1976 | Fujinami et al. |
| 4,394,930 | A | 7/1983 | Korpman |
| 4,547,195 | A | 10/1985 | Jackson |
| 4,715,857 | A * | 12/1987 | Juhasz ............. A61F 13/00029 602/42 |
| 4,744,374 | A | 5/1988 | Deffeyes et al. |
| 4,795,482 | A | 1/1989 | Gioffre et al. |
| 5,019,062 | A | 5/1991 | Baird et al. |
| 5,037,412 | A | 8/1991 | Tanzer et al. |
| 5,154,960 | A * | 10/1992 | Mucci ................. A61F 13/8405 428/68 |
| 5,161,686 | A | 11/1992 | Weber et al. |
| 5,221,274 | A | 6/1993 | Buell et al. |
| 5,256,159 | A | 10/1993 | Newman |
| 5,306,487 | A | 4/1994 | Karapasha et al. |
| 5,342,333 | A | 8/1994 | Tanzer et al. |
| 5,364,380 | A | 11/1994 | Tanzer et al. |
| 5,407,442 | A | 4/1995 | Karapasha |
| 5,423,786 | A | 6/1995 | Fung et al. |
| 5,429,628 | A | 7/1995 | Trinh et al. |
| H1579 | H | 8/1996 | Furio |
| 5,554,145 | A | 9/1996 | Roe et al. |
| 5,569,234 | A | 10/1996 | Buell et al. |
| 5,580,411 | A | 12/1996 | Nease et al. |
| 5,599,335 | A | 2/1997 | Goldman et al. |
| 5,637,105 | A | 6/1997 | Tanaka et al. |
| 5,693,385 | A | 12/1997 | Parks |
| 5,700,254 | A | 12/1997 | McDowall et al. |
| 5,714,445 | A | 2/1998 | Trinh et al. |
| 5,733,272 | A | 3/1998 | Trinh et al. |
| H1732 | H | 6/1998 | Johnson |
| 5,763,067 | A | 6/1998 | Bruggemann et al. |
| 5,769,832 | A | 6/1998 | Hasse |
| 5,769,833 | A | 6/1998 | Hasse |
| 5,834,114 | A | 11/1998 | Economy et al. |
| 5,837,627 | A | 11/1998 | Halabisky et al. |
| 5,843,267 | A | 12/1998 | Cashaw et al. |
| 5,922,163 | A | 7/1999 | Helynranta et al. |
| 5,944,704 | A | 8/1999 | Guarracino et al. |
| 5,951,534 | A | 9/1999 | Cummings et al. |
| 6,004,306 | A | 12/1999 | Robles et al. |
| 6,083,347 | A | 7/2000 | Thebrin et al. |
| 6,096,299 | A | 8/2000 | Guarracino et al. |
| 6,175,056 | B1 | 1/2001 | Carlucci et al. |
| 6,225,524 | B1 | 5/2001 | Guarracino et al. |
| 6,368,609 | B1 | 4/2002 | Fontenot et al. |
| 6,417,424 | B1 | 7/2002 | Bewick-Sonntag et al. |
| 6,426,445 | B1 * | 7/2002 | Young ................. A43B 1/0036 428/317.9 |
| 6,517,906 | B1 | 2/2003 | Economy et al. |
| 6,573,212 | B2 | 6/2003 | McCrae et al. |
| 6,617,490 | B1 | 9/2003 | Chen et al. |
| 6,653,521 | B1 | 11/2003 | Kurata et al. |
| 6,657,098 | B1 | 12/2003 | Niki et al. |
| 6,673,982 | B1 | 1/2004 | Chen et al. |
| 6,740,406 | B2 | 5/2004 | Hu et al. |
| 6,803,033 | B2 | 10/2004 | McGee et al. |
| 6,960,655 | B2 | 11/2005 | Di Cintio et al. |
| 6,972,010 | B2 | 12/2005 | Meo et al. |
| 7,234,648 | B2 | 6/2007 | Tepper et al. |
| 7,473,817 | B1 * | 1/2009 | Tanaka ............... A61F 13/8405 442/121 |
| 7,655,829 | B2 | 2/2010 | Macdonald et al. |
| 7,718,249 | B2 | 5/2010 | Russell et al. |
| 7,837,663 | B2 | 11/2010 | Macdonald et al. |
| 7,858,841 | B2 | 12/2010 | Krautkramer et al. |
| 7,919,666 | B2 | 4/2011 | Odorzynski |
| 8,058,500 | B2 | 11/2011 | Sojka et al. |
| 8,217,220 | B2 | 7/2012 | Berland et al. |
| 8,598,052 | B2 | 12/2013 | Suzuki et al. |
| 2001/0010852 | A1 | 8/2001 | Cotton et al. |
| 2001/0024716 | A1 | 9/2001 | Chen et al. |
| 2002/0052587 | A1 | 5/2002 | Magnusson et al. |
| 2002/0141961 | A1 | 10/2002 | Falat et al. |
| 2003/0003138 | A1 | 1/2003 | Di Cintio et al. |
| 2003/0012810 | A1 | 1/2003 | Di Cintio et al. |
| 2003/0018312 | A1 | 1/2003 | Pesce et al. |
| 2003/0023216 | A1 | 1/2003 | Carlucci et al. |
| 2003/0049480 | A1 | 3/2003 | Gagliardini et al. |
| 2003/0113289 | A1 | 6/2003 | Hu et al. |
| 2003/0124171 | A1 | 7/2003 | Sun et al. |
| 2003/0135172 | A1 | 7/2003 | Whitmore et al. |
| 2003/0144637 | A1 | 7/2003 | Sun et al. |
| 2003/0171726 | A1 | 9/2003 | Onishi et al. |
| 2004/0024092 | A1 | 2/2004 | Soerens et al. |
| 2004/0037861 | A1 | 2/2004 | Numano et al. |
| 2004/0067214 | A1 * | 4/2004 | Krautkramer ..... A61F 13/47218 424/76.3 |
| 2004/0121681 | A1 | 6/2004 | Lindsay et al. |
| 2004/0121682 | A1 | 6/2004 | Quincy et al. |
| 2004/0121688 | A1 | 6/2004 | Edens et al. |
| 2004/0122385 | A1 | 6/2004 | Morman et al. |
| 2004/0122386 | A1 | 6/2004 | Mocadlo |
| 2004/0122387 | A1 | 6/2004 | Long et al. |
| 2004/0122388 | A1 | 6/2004 | Mccormack et al. |
| 2004/0127867 | A1 | 7/2004 | Odorzynski et al. |
| 2004/0157971 | A1 | 8/2004 | Tung et al. |
| 2004/0166248 | A1 | 8/2004 | Hu et al. |
| 2005/0113771 | A1 | 5/2005 | Macdonald et al. |
| 2005/0148268 | A1 | 7/2005 | Tai |
| 2005/0159719 | A1 * | 7/2005 | Kawakami .......... A61F 13/8405 604/360 |
| 2005/0182376 | A1 | 8/2005 | Fleming |
| 2005/0192365 | A1 | 9/2005 | Strandburg et al. |
| 2006/0025731 | A1 | 2/2006 | Cohen |
| 2006/0030828 | A1 | 2/2006 | Wilhelm et al. |
| 2006/0129118 | A1 | 6/2006 | Mocadlo |
| 2006/0137568 | A1 | 6/2006 | Macdonald et al. |
| 2006/0140902 | A1 | 6/2006 | Macdonald et al. |
| 2006/0142709 | A1 | 6/2006 | Quincy, III |
| 2006/0142712 | A1 | 6/2006 | Quincy, III |
| 2006/0247590 | A1 | 11/2006 | Ito et al. |
| 2007/0043330 | A1 * | 2/2007 | Lankhof ............. A61F 13/531 604/378 |
| 2007/0073255 | A1 | 3/2007 | Thomas et al. |
| 2007/0077428 | A1 | 4/2007 | Hamed et al. |
| 2007/0270070 | A1 | 11/2007 | Hamed |
| 2008/0071238 | A1 | 3/2008 | Sierri et al. |
| 2008/0147028 | A1 | 6/2008 | Luna et al. |
| 2008/0147029 | A1 | 6/2008 | Pate et al. |
| 2008/0249490 | A1 | 10/2008 | Carlucci et al. |
| 2008/0300557 | A1 | 12/2008 | Forsgren et al. |
| 2008/0312572 | A1 | 12/2008 | Riesinger |
| 2008/0312622 | A1 | 12/2008 | Hundorf et al. |
| 2009/0024101 | A1 | 1/2009 | Toshishige et al. |
| 2009/0105676 | A1 | 4/2009 | Forsgren et al. |
| 2009/0157021 | A1 | 6/2009 | Sullivan et al. |
| 2009/0240220 | A1 | 9/2009 | Macdonald et al. |
| 2010/0080834 | A1 | 4/2010 | Lori et al. |
| 2010/0125261 | A1 | 5/2010 | Watson et al. |
| 2011/0112496 | A1 | 5/2011 | Fukae et al. |
| 2012/0058074 | A1 | 3/2012 | Braig et al. |
| 2012/0089067 | A1 | 4/2012 | Zhou et al. |
| 2012/0197226 | A1 | 8/2012 | Nakatani |
| 2012/0219728 | A1 * | 8/2012 | Badri ................ A61F 13/42 427/578 |
| 2012/0232511 | A1 | 9/2012 | Velazquez et al. |
| 2012/0258853 | A1 | 10/2012 | Veeraraghavan et al. |
| 2012/0277713 | A1 | 11/2012 | Raycheck et al. |
| 2013/0030340 | A1 | 1/2013 | Vincent et al. |
| 2013/0158491 | A1 * | 6/2013 | Caputi ................ A61F 13/5611 604/359 |
| 2013/0164334 | A1 | 6/2013 | Quincy, III et al. |
| 2013/0237933 | A1 | 9/2013 | Ko |
| 2014/0121619 | A1 | 5/2014 | Aslan-Guerel et al. |

(56) References Cited

U.S. PATENT DOCUMENTS

| | | | |
|---|---|---|---|
| 2014/0163506 A1* | 6/2014 | Roe | A61F 13/49001 604/378 |
| 2014/0243768 A1* | 8/2014 | Sa | A61L 15/46 604/359 |
| 2015/0246153 A1 | 9/2015 | Ota et al. | |
| 2015/0282999 A1* | 10/2015 | Arizti | A61F 13/51113 604/385.06 |
| 2015/0290052 A1 | 10/2015 | Forsgren et al. | |
| 2016/0151213 A1* | 6/2016 | Bauduin | A61F 13/532 604/365 |
| 2016/0338884 A1* | 11/2016 | Quincy | A61L 9/014 |
| 2017/0021051 A1* | 1/2017 | Richards | A61F 13/534 |
| 2017/0027778 A1* | 2/2017 | Stridfeldt | A61F 13/53747 |

FOREIGN PATENT DOCUMENTS

| | | |
|---|---|---|
| CN | 2082090 | 8/1991 |
| CN | 2197032 | 5/1995 |
| CN | 2205712 | 8/1995 |
| CN | 2350026 | 11/1999 |
| CN | 2506234 | 8/2002 |
| CN | 1380111 | 11/2002 |
| CN | 1126570 | 11/2003 |
| CN | 2655853 | 11/2004 |
| CN | 1559370 | 1/2005 |
| CN | 2680230 | 2/2005 |
| CN | 2694943 | 4/2005 |
| CN | 1698561 | 11/2005 |
| CN | 2756191 | 2/2006 |
| CN | 1757808 | 4/2006 |
| CN | 2838580 | 11/2006 |
| CN | 2848196 | 12/2006 |
| CN | 1899231 | 1/2007 |
| CN | 101036800 | 9/2007 |
| CN | 200948202 | 9/2007 |
| CN | 201061588 | 5/2008 |
| CN | 101229390 | 7/2008 |
| CN | 201079505 | 7/2008 |
| CN | 201079506 | 7/2008 |
| CN | 101273938 | 10/2008 |
| CN | 201182688 | 1/2009 |
| CN | 101417143 | 4/2009 |
| CN | 201227436 | 4/2009 |
| CN | 201248805 | 6/2009 |
| CN | 201283041 | 8/2009 |
| CN | 201304040 | 9/2009 |
| CN | 201316359 | 9/2009 |
| CN | 101569583 | 11/2009 |
| CN | 201399048 | 2/2010 |
| CN | 201631505 | 11/2010 |
| CN | 201643065 | 11/2010 |
| CN | 201768080 | 3/2011 |
| CN | 102068715 | 5/2011 |
| CN | 201883331 | 6/2011 |
| CN | 201959109 | 9/2011 |
| CN | 202060984 | 12/2011 |
| CN | 102327641 | 1/2012 |
| CN | 202235945 | 5/2012 |
| CN | 202235949 | 5/2012 |
| CN | 202554262 | 11/2012 |
| CN | 102813955 | 12/2012 |
| CN | 102813959 | 12/2012 |
| CN | 102813960 | 12/2012 |
| CN | 202637281 | 1/2013 |
| CN | 202637282 | 1/2013 |
| CN | 202776752 | 3/2013 |
| CN | 202933105 | 5/2013 |
| CN | 203169434 | 9/2013 |
| CN | 103340722 | 10/2013 |
| CN | 103349592 | 10/2013 |
| CN | 103356334 | 10/2013 |
| CN | 203447630 | 2/2014 |
| CN | 203458534 | 3/2014 |
| DE | 3816352 | 11/1989 |
| DE | 4118608 | 12/1992 |
| DE | 29510390 | 12/1995 |
| DE | 4429251 | 2/1996 |
| DE | 19603840 | 8/1997 |
| DE | 19816393 | 10/1999 |
| DE | 19929106 | 12/2000 |
| DE | 19939902 | 3/2001 |
| DE | 202006005874 | 7/2006 |
| DE | 202013105048 | 1/2014 |
| EP | 0041569 | 12/1981 |
| EP | 0263975 | 9/1987 |
| EP | 0389015 | 9/1990 |
| EP | 0389023 | 9/1990 |
| EP | 0510619 | 10/1992 |
| EP | 0592001 | 4/1994 |
| EP | 0811389 | 12/1997 |
| EP | 0811390 | 12/1997 |
| EP | 0811392 | 12/1997 |
| EP | 0850615 | 7/1998 |
| EP | 0850623 | 7/1998 |
| EP | 0933086 | 8/1999 |
| EP | 0933088 | 8/1999 |
| EP | 1034800 | 9/2000 |
| EP | 1034801 | 9/2000 |
| EP | 1118340 | 7/2001 |
| EP | 1358894 | 11/2003 |
| EP | 1447066 | 8/2004 |
| EP | 1884251 | 2/2008 |
| FR | 1272233 | 9/1961 |
| FR | 2331603 | 6/1977 |
| GB | 2093351 | 9/1982 |
| GB | 2292526 | 2/1996 |
| IN | 197126 | 8/2006 |
| JP | 5161671 | 6/1993 |
| JP | 9176965 | 7/1997 |
| JP | 11104179 | 4/1999 |
| JP | 2000175963 | 6/2000 |
| JP | 2000201972 | 7/2000 |
| JP | 2000201973 | 7/2000 |
| JP | 2000318108 | 11/2000 |
| JP | 2001037805 | 2/2001 |
| JP | 2001145648 | 5/2001 |
| JP | 2001231816 | 8/2001 |
| JP | 2003052746 | 2/2003 |
| JP | 2003260082 | 9/2003 |
| JP | 2004215693 | 8/2004 |
| JP | 2009106464 | 5/2009 |
| JP | 4651392 | 3/2011 |
| JP | 4667485 | 4/2011 |
| JP | 5368829 | 12/2013 |
| JP | 2014068680 | 4/2014 |
| JP | 2014068681 | 4/2014 |
| KR | 930008910 B1 | 9/1993 |
| KR | 20010070751 | 7/2001 |
| KR | 20030054460 | 7/2003 |
| KR | 20030054462 | 7/2003 |
| KR | 20030064631 | 8/2003 |
| KR | 20040062479 | 7/2004 |
| KR | 20040066635 | 7/2004 |
| KR | 20050099105 | 10/2005 |
| KR | 101008171 | 1/2011 |
| KR | 20110049432 | 5/2011 |
| TH | 10504 B | 5/2001 |
| TH | 10505 B | 5/2001 |
| WO | WO8204271 | 12/1982 |
| WO | WO9111977 | 8/1991 |
| WO | WO9112030 | 8/1991 |
| WO | WO 95/10996 | 4/1995 |
| WO | WO 95/11652 | 5/1995 |
| WO | WO9736047 | 10/1997 |
| WO | WO9746187 | 12/1997 |
| WO | WO9746192 | 12/1997 |
| WO | WO9826808 | 6/1998 |
| WO | WO9827912 | 7/1998 |
| WO | WO9906078 | 2/1999 |
| WO | WO0016816 | 3/2000 |
| WO | WO 2000/59430 | 10/2000 |
| WO | WO0062826 | 10/2000 |
| WO | WO 02/067809 | 9/2002 |

(56) References Cited

FOREIGN PATENT DOCUMENTS

| | | |
|---|---|---|
| WO | WO02091976 | 11/2002 |
| WO | WO02094329 | 11/2002 |
| WO | WO2003002089 | 1/2003 |
| WO | WO2003002164 | 1/2003 |
| WO | WO2004060418 | 7/2004 |
| WO | WO2007067110 | 6/2007 |
| WO | WO2007/113778 | 10/2007 |
| WO | WO 2011/063370 | 5/2011 |
| WO | WO 2012/052172 | 4/2012 |
| WO | WO2012163995 | 12/2012 |
| WO | WO2014019813 | 2/2014 |
| WO | WO2014033589 | 3/2014 |
| WO | WO2014035306 | 3/2014 |
| WO | WO 2015/094068 | 6/2015 |

\* cited by examiner

ARTICLE COMPRISING ODOR CONTROL COMPOSITION

FIELD OF THE INVENTION

The present invention relates to absorbent articles comprising an odor control composition and methods of making and using same.

BACKGROUND OF THE INVENTION

Unscented or low scented products are desired by consumers as they may be considered more natural and discreet than scented products. Manufacturers of unscented or low scented products for controlling odors rely on odor reduction ingredients or other technologies (e.g. filters) to reduce malodors. But some of the odor control compositions, while known to be effective, may not be visually attractive when incorporated into the product. Therefore, there is a continuing need for ways to control or reduce unwanted odors while maintaining an attractive appearance of the product.

SUMMARY OF THE INVENTION

Described herein are disposable absorbent articles having a longitudinal centerline and a lateral centerline, a front waist region with a front waist edge, a rear waist region with a rear waist edge, a crotch region disposed between said front and rear waist regions and two spaced apart longitudinal side edges joining said front waist edge to said rear waist edge and comprising an assembly of components including: a topsheet; a backsheet underlying said topsheet; an absorbent core disposed between said topsheet and said backsheet, the absorbent core comprising a core wrap; a liquid management system disposed between the topsheet and the absorbent core; wherein an odor control composition is placed between the core wrap and the liquid management system; and wherein the core wrap has a surface area facing the liquid management system, and the odor control composition is placed over at most about 80% of the core wrap surface area.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting examples of the disclosure taken in conjunction with the accompanying drawings, wherein.

DETAILED DESCRIPTION OF THE INVENTION

Definitions

Figure 1:
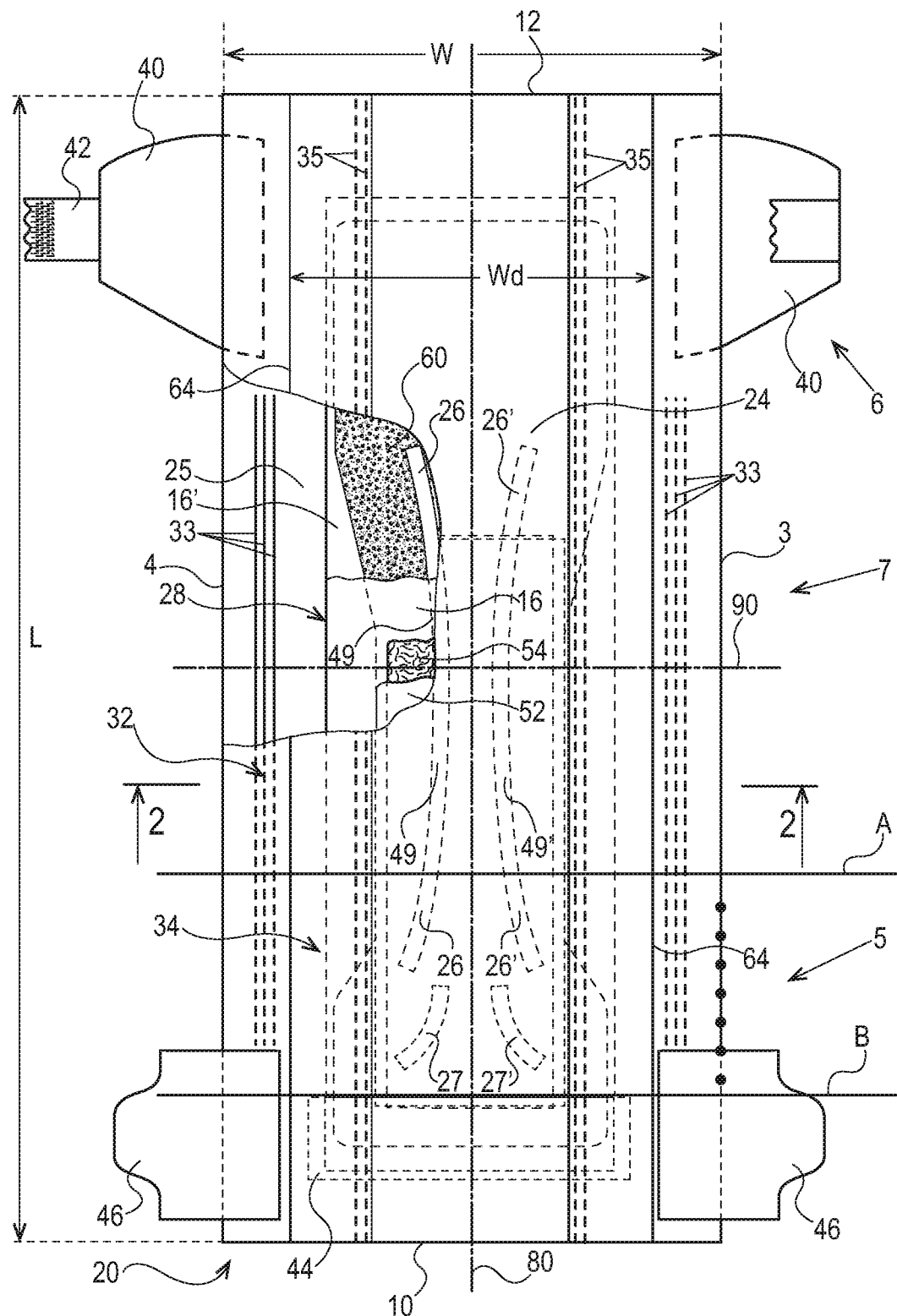
FIG. 1 is a top view of an absorbent article with some layers partially removed in accordance with the present disclosure.

The term "absorbent article, as used herein, refers to disposable devices such as infant, child, or adult diapers, sanitary napkins, adult incontinence products, pant-style diapers, training pants, diaper inserts, and the like which are placed against or in proximity to the body of the wearer to absorb and contain the bodily exudates (e.g., urine and BM) discharged from the body. Typically, these articles comprise a topsheet, backsheet, an absorbent core, optionally a liquid management system (LMS), and typically other components, with the absorbent core normally placed at least partially between the backsheet and the LMS (if provided) or between the topsheet and the backsheet. The absorbent articles of the present disclosure will be further illustrated in the below description and in the Figures in the form of a taped diaper. Nothing in this description should be, however, considered to limit the scope of the claims. As such the present disclosure applies to any suitable form of absorbent articles (e.g., training pants, taped diapers, adult incontinence products—in either taped or pant forms, sanitary napkins).

"Adhesive" refers to compositions comprising one or more thermoplastic polymers and typically one or more tackifier resins and a rheology modifier or plasticizer. Adhesives may contain 2% or more of a tackifier resin. An adhesive is generally used to join or bond two or more materials together by applying it to at least one material and then bringing it into contact with at least one other material with sufficient force and for a sufficient duration of time, that the adhesive can wet out or spread on each material to join them together (see definition of "tackifier" below).

As used herein "consumer product" means baby care and/or feminine care products or devices intended to be used or consumed in the form in which it is sold, and not intended for subsequent commercial manufacture or modification. Such products include but are not limited to diapers, bibs, wipes; skin care including application of creams, lotions, and other topically applied products for consumer use; tampons and/or feminine napkins.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable" in reference to absorbent articles, means that the absorbent articles are generally not intended to be laundered or otherwise restored or reused as absorbent articles (i.e., they are intended to be discarded after a single use and may be recycled, composted or otherwise discarded in an environmentally compatible manner).

As used herein, "malodor" refers to compounds generally offensive or unpleasant to most people, such as the complex odors associated with bowel movements.

As used herein, "neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Neutralization is distinguishable from odor masking or odor blocking by a change in the malodorous compound, as opposed to a change in the ability to perceive the malodor without any corresponding change in the condition of the malodorous compound. Malodor neutralization provides a sensory and analytically measurable (e.g. gas chromatograph) malodor reduction. Thus, if a malodor reduction composition delivers genuine malodor neutralization, the composition will reduce malodors in the vapor and/or liquid phase.

The term "nonwoven web", as used herein, means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, and airlaying. The basis weight of nonwoven webs is usually expressed in grams per square meter (g/m$^2$ or gsm).

The terms "join", "joined" "joining", "bond", "bonding", "bonded", "attach", "attached", or "attaching" as used herein, encompasses configurations whereby an element is directly secured to another element by affixing the element directly to the other element, and configurations whereby an element is indirectly secured to another element by affixing the element to intermediate member(s) which in turn are affixed to the other element.

As used herein, "odor masking" refers to the ability of a compound with a non-offensive or pleasant smell that is dosed such that it limits the ability to sense a malodorous compound. Odor-masking may involve the selection of compounds that coordinate with an anticipated malodor to change the perception of the overall scent provided by the combination of odorous compounds.

"Tackifier" refers to an adhesive component with a glass transition temperature in the range from about 70° C. to about 150° C. that decreases the melt viscosity of a rubbery polymer and increases the rubbery polymer's glass transition temperature and decreases the rubbery polymer's entanglement density.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force.

As used herein, the term "nonelastic" refers to any material which does not fall within the definition of "elastic" above.

As used herein, the term "extensible" refers to any material which, upon application of a biasing force, is elongatable, at least about 50 percent, at least about 100%, or at least about 125%, without experiencing catastrophic failure.

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened).

As used herein, the terms "a" and "an" mean "at least one".

As used herein, the terms "include", "includes" and "including" are meant to be non-limiting. Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Odor Control Compositions

There are numerous types of odor control compositions that may be effective in the present invention. Some examples of suitable odor control compositions include, but are not limited to, activated carbon, colored activated carbon, zeolites, silica, clays (e.g., smectite clay), alumina, magnesia, titania, chitin, ion exchange resins, cyclodextrins, tenax (2,6-diphenylphenylene oxide), and combinations thereof. For instance, activated carbon may be derived from a variety of sources, such as from sawdust, wood, charcoal, peat, lignite, bituminous coal, coconut shells, etc. Some suitable forms of activated carbon and techniques for formation thereof are described in U.S. Pat. No. 5,693,385 to Parks; U.S. Pat. No. 5,834,114 to Economy, et al.; U.S. Pat. No. 6,517,906 to Economy, et aL; U.S. Pat. No. 6,573,212 to McCrae. et al. as well as U.S. Patent Application Publication Nos. 2002/0141961 to Falat, et al. and 2004/0166248 to Hu. et al.

The carbon material suitable for employment herein is the material well known in the art as an absorber for organic molecules and/or air purification purposes. Carbon suitable for use herein is available from a number of commercial sources under the trade names such as CALGON Type "CPG", Type SGL, Type "CAL" and type "OL". Often such material is referred to as "activated" carbon or "activated" charcoal. Typically it is available in the form of extremely fine, dusty particles having large surface areas (200—several thousand $m^2/g$.) It is to be understood that any of the "air purifying" or "activated" carbons of commerce can be used in the practice of this invention. The amount of activated carbon that may be used per absorbent article may be from about 0.001 grams to about 10 grams (g), from about 0.001 g to about 5 g, from about 0.01 to 2 g, from about 0.05 g to about 2 g, from about 0.1 g to about 1 g, or from about 0.05 g to about 2 g. Activated carbon is described, for example, in the following reference text: *Activated Carbon Applications in the Food and Pharmaceutical Industries*, by Glenn M. Roy, Technomic Publishing Co., Inc. (1994).

The use and manufacture of zeolite material is well known in the literature and is described in the following reference texts: *Zeolite Synthesis*, ACS Symposium Series 398, Eds. M. L. Occelli and H. E Robson (1989) pages 2-7; *Zeolite Molecular Sieves*, Structure, Chemistry and Use, by D. W. Breck, John Wiley and Sons (1974) pages 245-250, 313-314 and 348-352; *Modern Applications of Molecular Sieve Zeolites*, Ph.D. Dissertation of S. M. Kuznicki, U. of Utah (1980), available from University of Microfilms International, Ann Arbor, Mich., pages 2-8.

Zeolites are crystalline aluminosilicates of group IA and group IIA elements such as Na, K, Mn, Ca and are chemically represented by the empirical formula: $M_2/nO$, $Al_2O_3$, $ySiO_2$, $wH_2O$, where y is 2 or greater, n is the cation valence, and w is the water content in the voids of the zeolite. Structurally, zeolites are complex, crystalline inorganic polymers based on an infinitely extending framework of $AlO_4$ and $SiO_4$ tetrahedra linked to each other by sharing of oxygen ions. This framework structure contains channels or interconnected voids that are occupied by the cations and water molecules.

The structural formula of a zeolite is based on the crystal unit cell, the smallest unit of structure, represented by $M_{x/n}[(AlO_2)_x(SiO_2)_y] \cdot wH_2O$ where n is the valence of cation M, w is the number of water molecules per unit cell, x and y are the total number of tedrahedra per unit cell, y/x usually having values of 1-5.

Zeolites may be naturally derived or synthetically manufactured. The synthetic zeolites being preferred for use herein. Suitable zeolites for use herein include zeolite A, zeolite P, zeolite Y, zeolite X, zeolite DAY, zeolite ZSM-5, or mixtures thereof. Most preferred are zeolite A and zeolite Y or mixtures thereof. The zeolite may be hydrophobic. This is typically achieved by increasing the molar ratio of the $SiO_2$ to $AlO_2$ content such that the ratio of x to y is at least 1, preferably from 1 to 500, most preferably from 1 to 6. The absorbent article may comprise from 40 $gm^{-2}$ to 90 $gm^{-2}$, in some embodiments from 55 $gm^{-2}$ to 85 $gm^{-2}$, and in other embodiments from 60 $gm^{-2}$ to 65 $gm^{-2}$ of said zeolite.

The present invention the odor control composition may comprise silica. Silica, i.e. silicon dioxide $SiO_2$, exists in a variety of crystalline forms and amorphous modifications, any of which are suitable for use herein. Silicas tend to have a high surface area, and the silica may be in agglomerated form. The silica may be in a highly purified form such that it contains at least about 90%, about 95%, or even about 99% silicon dioxide. The silica may be silica gel having 100% silica content. Alternatively, the silica may be provided from other sources such as metal silicates including sodium silicate. The absorbent article preferably comprises from about 40 $gm^{-2}$ to about 100 $gm^{-2}$, in some cases from 60 $gm^{-2}$ to 90 $gm^{-2}$, in other cases from about 60 $gm^{-2}$ to about 65 $gm^{-2}$ of silica based on 100% purity.

In some embodiments, the odor control composition may be in particulate form, such as a molecular sieve material (generally in the size range of 1-5 micrometers). The amount of the particulate may be from about 0.001 g to about 5 g, or in some embodiments from about 0.05 g to about 1 g. The particulates may be applied to the article in the form of an aqueous slurry containing the particulate odor control composition, a binding agent, a wetting agent, and so forth. Illustrative binding agents include polyvinyl alcohol, methyl cellulose, carboxy methyl cellulose, starch (including ethylated and oxidized derivatives thereof), and various polymer emulsions. The slurry may be applied in the desired pattern by various techniques, such as print (including screen printing), spraying, contact coated, blade, saturant, coating, droplet throw, paint, and foam applications. EP 392,528 describes methods of applying a slurry containing a particulate odor control composition to a web material of an absorbent article. The odor control composition may be incorporated directly into a fiber or nonwoven substrate component of the article. That is, the odor control composition may be in the form of a substrate, for example, a tissue or fabric that is impregnated with a particular odor control composition, such as activated carbon. The substrate may be a nonwoven or cellulose-based material, and may be any of the appropriate article components described herein. In some embodiments, the odor control composition may be in the form of a pouch or sachet, which can be a nonwoven pouch or sachet comprising the odor control composition. In some embodiments, the odor control composition may be a laminate or a film.

Article

Figure 2:
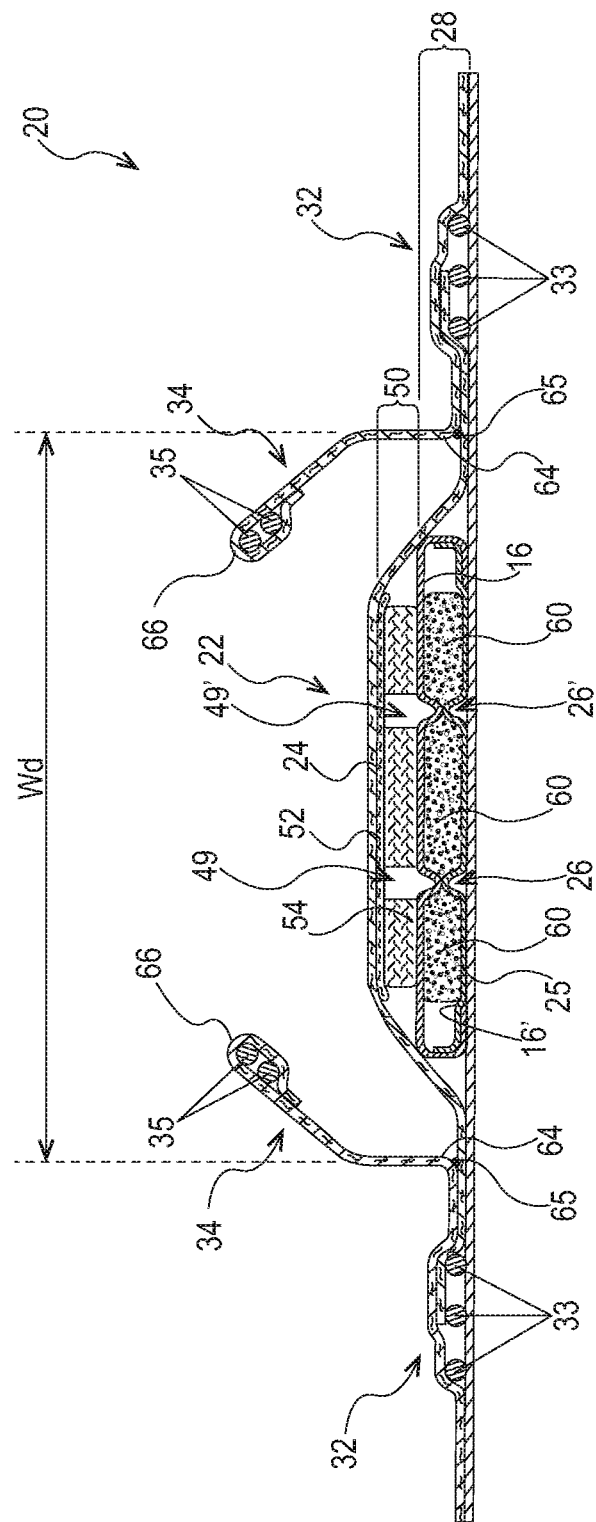
FIG. 2 is a cross-sectional view of the absorbent article taken about line 2-2 of FIG. 1 in accordance with the present disclosure.
Figure 3:
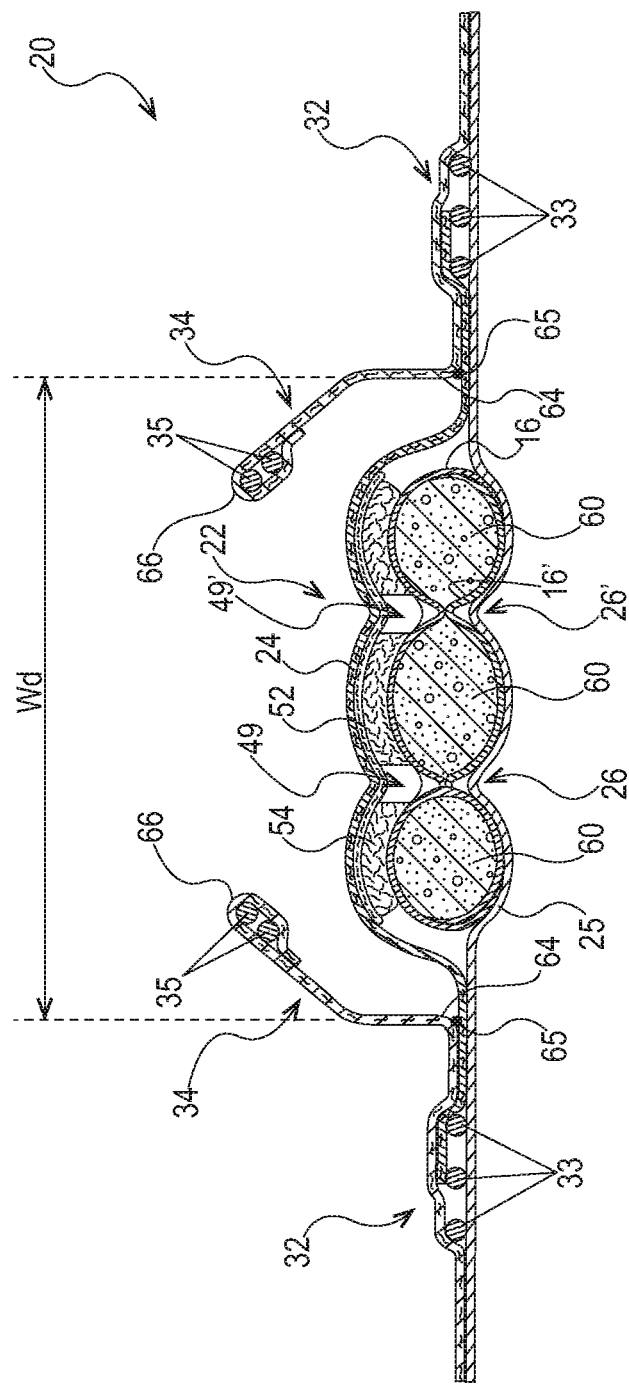
FIG. 3 is a view of the absorbent article of FIG. 2 where the absorbent article has been at least partially loaded with fluid in accordance with the present disclosure.

An example absorbent article 20 according to the present disclosure, shown in the form of a diaper, is represented in FIGS. 1-3. FIG. 1 is a plan view of the diaper, in a flat-out state, wearer-facing surface toward the viewer, with portions of the structure being cut-away to more clearly show the construction of the diaper. This diaper is shown for illustration purpose only as the present disclosure may be used for making a wide variety of diapers and other absorbent articles.

The absorbent article may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise a liquid management system ("LMS") 50 (shown in FIG. 2), which, in the example represented, comprises a distribution layer 54 and an acquisition layer 52 that will both be further discussed below. In various forms, the acquisition layer 52 may instead distribute bodily exudates and the distribution layer 54 may instead acquire bodily exudates or both layers may distribute and/or acquire bodily exudates. The LMS 50 may also be provided as a single layer or two or more layers. The absorbent article may also comprise elasticized gasketing cuffs 32 or 33 joined to the chassis of the absorbent article, typically via the topsheet and/or backsheet, and substantially planar with the chassis of the diaper.

The Figures also show typical taped diaper components such as a fastening system comprising adhesive tabs 42 or other mechanical fasteners attached towards the rear edge of the absorbent article 20 and cooperating with a landing zone 44 on the front of the absorbent article 20. The absorbent article may also comprise other typical elements, which are not represented, such as a rear elastic waist feature and a front elastic waist feature, for example.

The absorbent article 20 may comprise a front waist edge 10, a rear waist edge 12 longitudinally opposing the front waist edge 10, a first side edge 3, and a second side edge 4 laterally opposing the first side edge 3. The front waist edge 10 is the edge of the absorbent article 20 which is intended to be placed towards the front of the user when worn, and the rear waist edge 12 is the opposite edge. Together the front waist edge 10 and the rear waist edge form waist opening when the absorbent article 20 is donned on a wearer. The absorbent article 20 may have a longitudinal axis 80 extending from the lateral midpoint of the front waist edge 10 to a lateral midpoint of the rear waist edge 12 of the absorbent article 20 and dividing the absorbent article 20 in two substantially symmetrical halves relative to the longitudinal axis 80, with article placed flat and viewed from the wearer-facing surface as illustrated FIG. 1. The absorbent article may also have a lateral axis 90 extending from the longitudinal midpoint of the first side edge 3 to the longitudinal midpoint of the second side edge 4. The length L of the absorbent article 20 may be measured along the longitudinal axis 80 from the front waist edge 10 to the rear waist edge 12. The crotch width W of the absorbent article 20 may be measured along the lateral axis 90 from the first side edge 3 to the second side edge 4. The absorbent article 20 may comprise a front waist region 5, a rear waist region 6, and a crotch region 7. The front waist region, the rear waist region, and the crotch region each define ⅓ of the longitudinal length of the absorbent article. Front and back portions may also be defined on opposite sides of the lateral axis 90.

The topsheet 24, the backsheet 25, the absorbent core 28, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306.

The absorbent core 28 may comprise an absorbent material comprising 75% to 100%, at least 80%, at least 85%, at least 90%, at least 95%, or at least 99%, all by weight, of the absorbent material, specifically reciting all 0.1% increments within the above-specified ranges and all ranges formed therein or thereby, and a core wrap enclosing the absorbent material. The core wrap may typically comprise two materials, substrates, or nonwoven materials 16 and 16' (see FIG. 8) for the top side and bottom side of the core.

The absorbent core 28 may comprises one or more channels, represented in FIG. 1 as the four channels 26, 26' and 27, 27'. Additionally or alternatively, the LMS 50 may comprise one or more channels, represented in FIGS. 1-3 as channels 49, 49'. In some forms, the channels of the LMS 50 may be positioned within the absorbent article 20 such they aligned with, substantially aligned with, overlap, or at least partially overlap, the channels of the absorbent core 28.

These and other components of the absorbent articles will now be discussed in more details.

Topsheet

The topsheet 24 is the part of the absorbent article that is directly in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the article) and are indirectly joined together in other locations by directly joining them to one or more other elements of the absorbent article 20.

The topsheet 24 may be compliant, soft-feeling, and non-irritating to the wearer's skin. Further, at least a portion of the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, melt-blown, hydroentangled, or otherwise processed as is known in the art, in particular spunbond PP nonwoven.

Typical absorbent article topsheets have a basis weight of from about 5 gsm to about 50 gsm, from about 10 to about 35 gsm or from about 12 to about 30 gsm, but other basis weights are within the scope of the present disclosure.

Backsheet

The backsheet 25 is generally that portion of the absorbent article 20 positioned adjacent the garment-facing surface of the absorbent core 28 and which prevents, or at least inhibits, the bodily exudates absorbed and contained therein from soiling articles such as bedsheets and undergarments. The backsheet 25 is typically impermeable, or at least substantially impermeable, to liquids (e.g., urine, running BM), but permeable to vapors to allow the diaper to "breath". The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, bodily exudates from passing through the backsheet 25. Example breathable materials may include materials such as woven webs, nonwoven webs, composite materials such as film-coated nonwoven webs, microporous films, and monolithic films.

The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the absorbent article 20.

Absorbent Core

As used herein, the term "absorbent core" refers to the individual component of the absorbent article having the most absorbent capacity and that comprises an absorbent material. The absorbent core may comprise a core wrap or core bag (hereafter "core wrap") enclosing the absorbent material. The term "absorbent core" does not include the LMS or any other component of the absorbent article which is not either integral part of the core wrap or placed within the core wrap. The absorbent core may comprise, consist essentially of, or consist of, a core wrap, absorbent material as defined below, and glue enclosed within the core wrap. Pulp or air-felt may also be present within the core wrap and may form a portion of the absorbent material. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 28 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The SAP useful with the present disclosure may include a variety of water-insoluble, but water-swellable polymers capable of absorbing large quantities of fluids. The core wrap is not considered as absorbent material for the purpose of assessing the percentage of SAP in the absorbent core. The remainder of the absorbent material in the core 28 may be air-felt.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers or airfelt. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, cellulose and/or natural and/or synthetic fibers, specifically reciting all 0.1% increments within the specified ranges and all ranges formed therein or thereby. The absorbent material may comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

Figure 4:
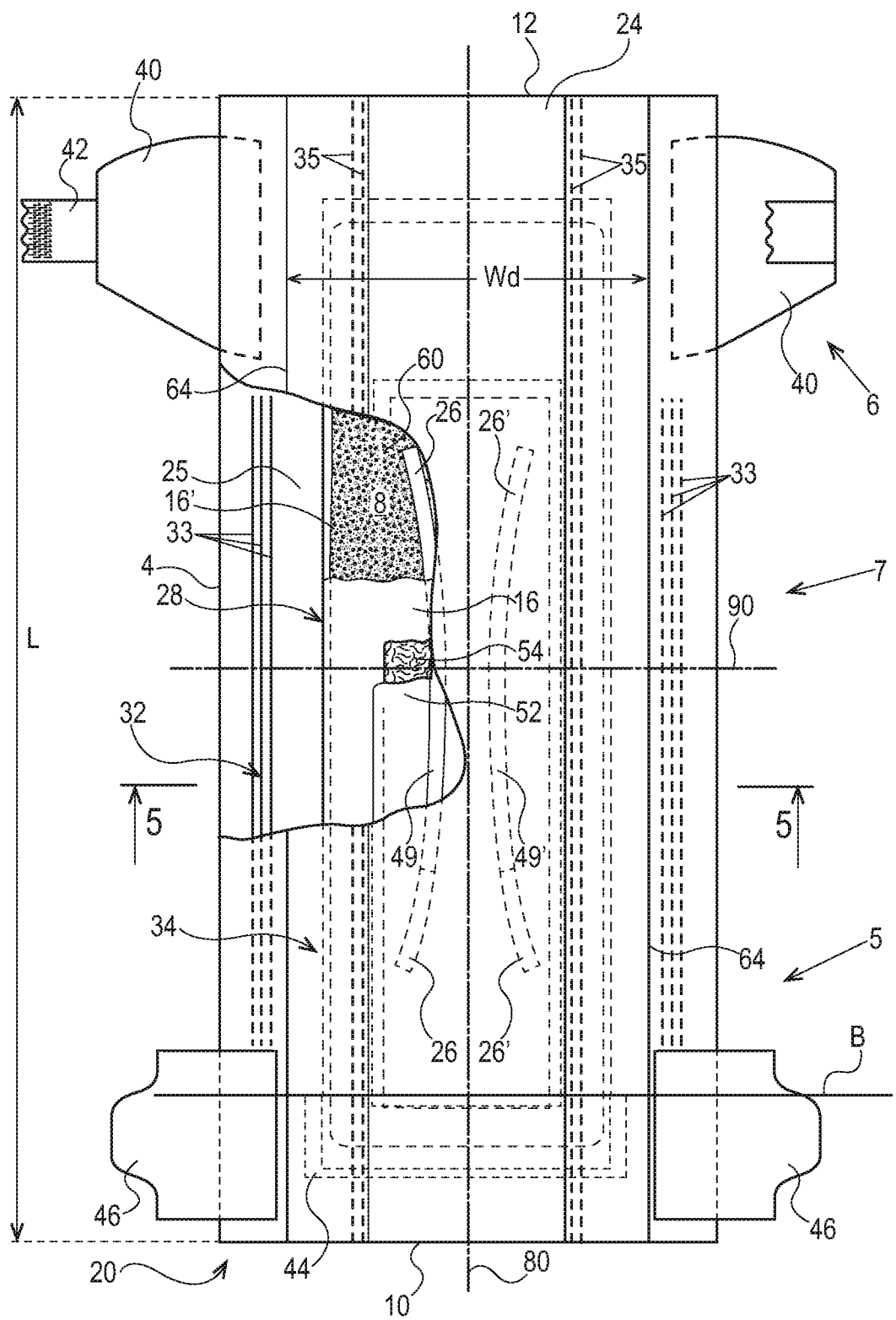
FIG. 4 is a top view of another absorbent article with some layers partially removed in accordance with the present disclosure.
Figure 5:
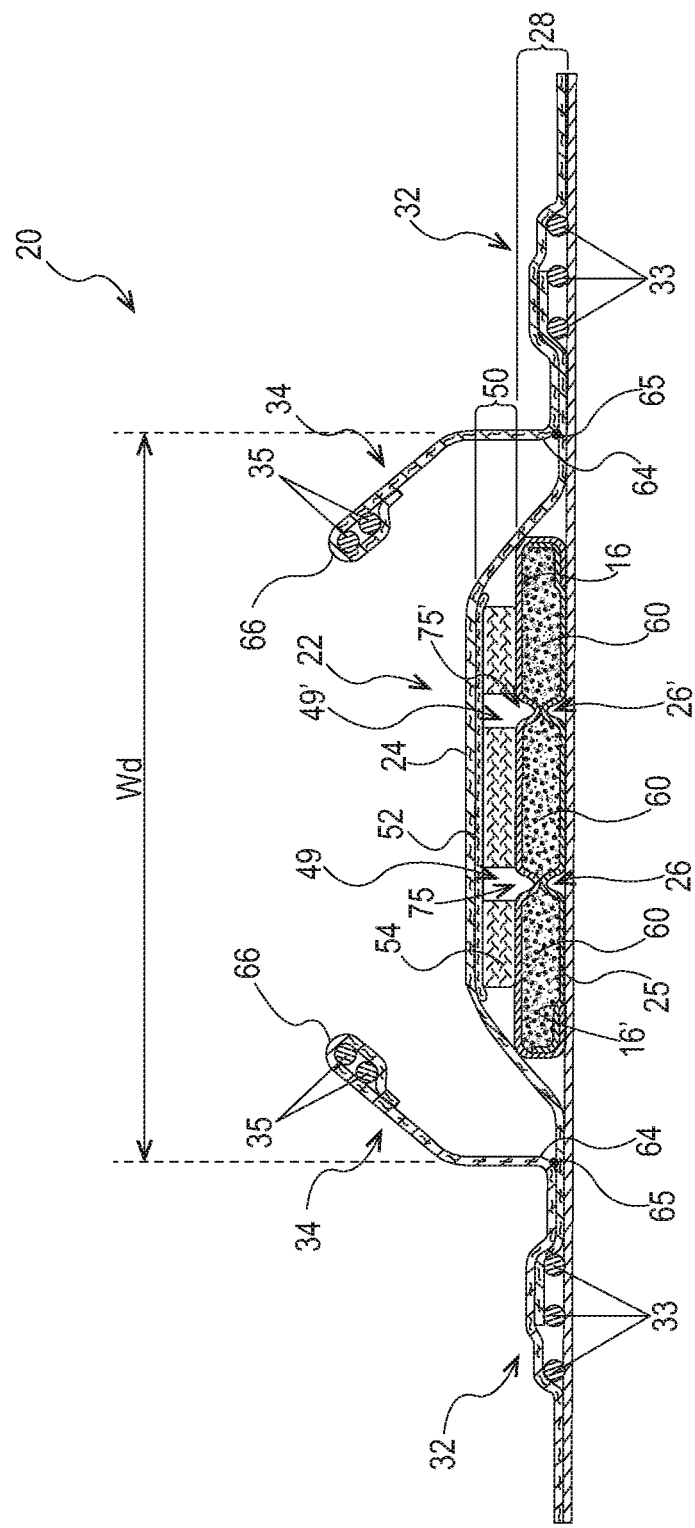
FIG. 5 is a cross-sectional view of the absorbent article taken about line 5-5 of FIG. 4 in accordance with the present disclosure.
Figure 6:
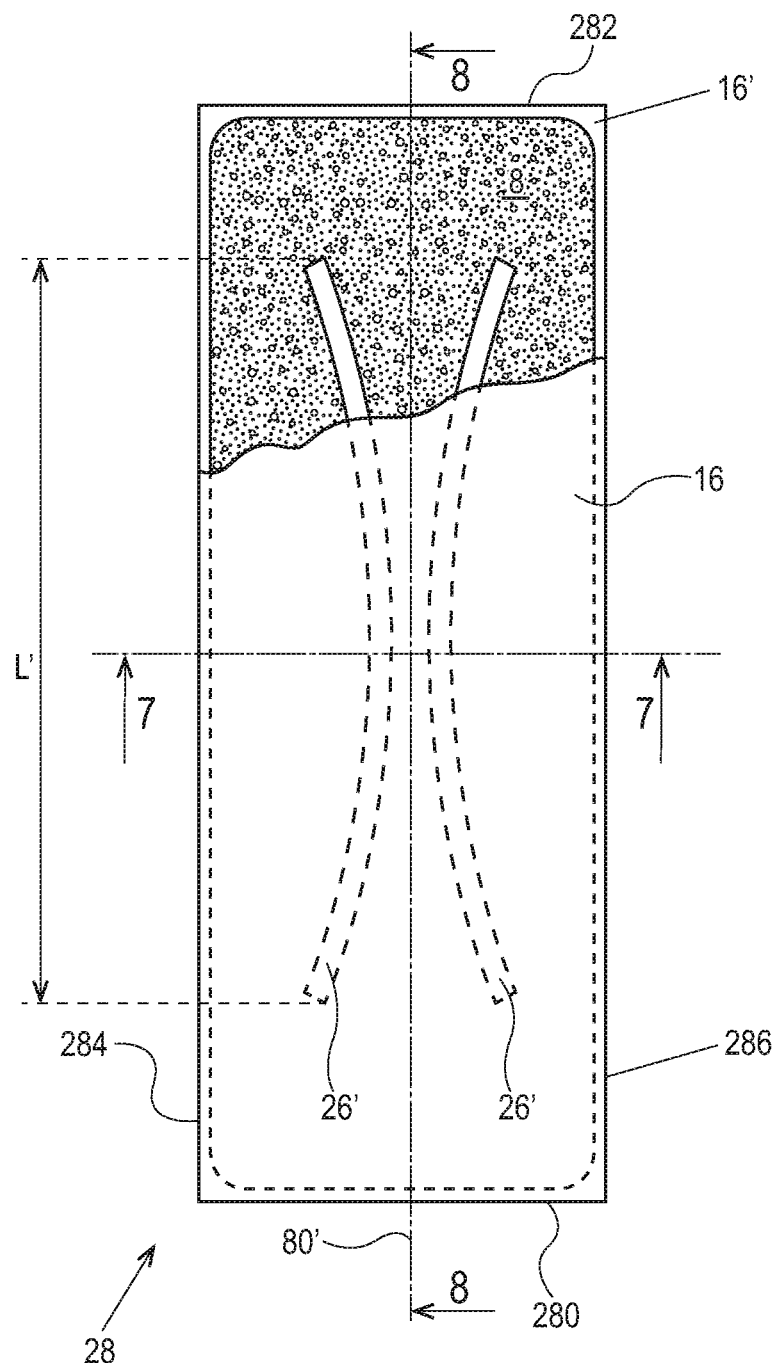
FIG. 6 is a top view of an absorbent core of the absorbent article of FIG. 4 with some layers partially removed in accordance with the present disclosure.
Figure 7:
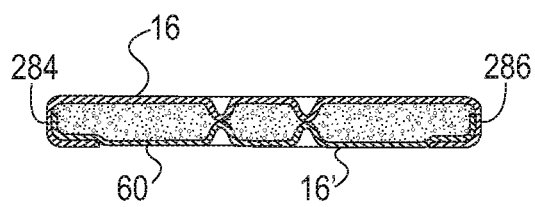
FIG. 7 is a cross-sectional view of the absorbent core taken about line 7-7 of FIG. 6 in accordance with the present disclosure.
Figure 8:
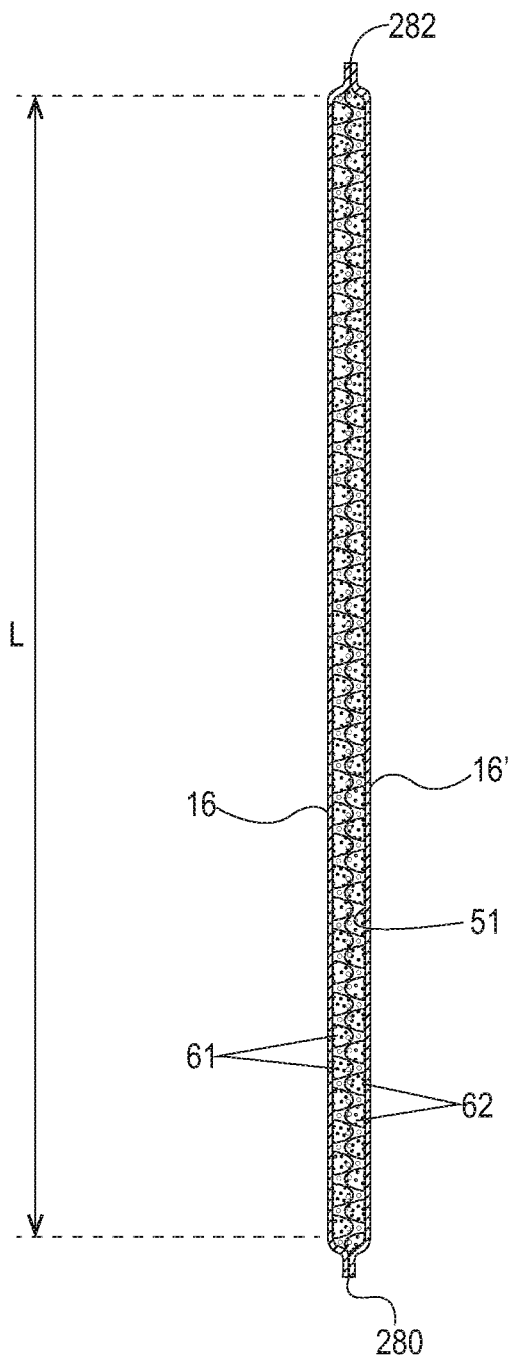
FIG. 8 is a cross-sectional view of the absorbent core taken about line 8-8 of FIG. 6 in accordance with the present disclosure.

The example absorbent core 28 of the absorbent article of FIGS. 4 and 5 is shown in isolation in FIGS. 6-8. The absorbent core 28 may comprise a front side 280, a rear side 282, and two longitudinal sides 284, 286 joining the front side 280 and the rear side 282. The absorbent core 28 may also comprise a generally planar top side and a generally planar bottom side. The front side 280 of the core 28 is the side of the core 28 intended to be placed towards the front waist edge 10 of the absorbent article. The core 28 may have a longitudinal axis 80' corresponding substantially to the longitudinal axis 80 of the absorbent article, as seen from the top in a planar view as in FIG. 1. The absorbent material may be distributed in higher amount towards the front side than towards the rear side as more absorbency may be required at the front in particular articles. The absorbent material may have a non-uniform basis weight or a uniform basis weight across any portion of the core. The core wrap may be formed by two nonwoven materials, substrates, laminates, or other materials, 16, 16' which may be at least partially sealed along the sides of the absorbent core. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. Alternatively, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 28 and bonded in that position.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may also be generally rectangular, for example as shown in FIGS. 4-6, but other deposition areas, such as a "T," "Y," "hour-glass," or "dog-bone" shapes are also within the scope of the present disclosure.

Channels in the Absorbent Core

The absorbent material deposition area 8 may comprise at least one channel 26, which is at least partially oriented in the longitudinal direction of the absorbent article 80 (i.e., has a longitudinal vector component). Other channels may be at least partially oriented in the lateral direction (i.e., has a lateral vector component) or in any other direction. In the following, the plural form "channels" will be used to mean "at least one channel". The channels may be circular, oblong, or be in the shape of a variety of other closed polygons. The channels may be formed in various ways. For example, the channels may be formed by zones within the absorbent material deposition area 8 which may be substantially free of, or free of, absorbent material, in particular, SAP. In addition or alternatively, the channels may also be formed by continuously or discontinuously bonding the top side of the core wrap to the bottom side of the core wrap through the absorbent material deposition area 8. The channels may be continuous or intermittent. The liquid management system 50, or another layer of the absorbent article, may also comprise channels, which may or not correspond to the channels of the absorbent core, as described in more detail below.

The absorbent core 28 may comprise more than two channels, for example, at least 3, at least 4, etc. Shorter channels may also be present, for example in the rear waist region 6 or the front waist region 5 of the core as represented by the pair of channels 27, 27' in FIG. 1 towards the front of the absorbent article 20. The channels may comprise one or more pairs of channels symmetrically arranged, or otherwise arranged relative to the longitudinal axis 80 or the lateral axis 90.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the a backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Absorbent cores and/or LMSs without any channels are also within the scope of the present disclosure. These cores may include airfelt-free cores, SAP/pulp cores, pulp cores, or other cores known to those of skill in the art.

Barrier Leg Cuffs

The absorbent article may comprise a pair of barrier leg cuffs 34. Each barrier leg cuff may be formed by a piece of material which is bonded to the absorbent article so it can extend upwards from the inner surface of the absorbent article and provide improved containment of liquids and other bodily exudates approximately at the junction of the torso and legs of the wearer. The barrier leg cuffs 34 are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present in the crotch region 7. The barrier leg cuffs 34 may be joined at the proximal edge 64 with the chassis of the absorbent article by a bond 65 which may be made by gluing, fusion bonding, or combination of other suitable bonding processes. The bond 65 at the proximal edge 64 may be continuous or intermittent. The bond 65 closest to the raised section of the leg cuffs 34 delimits the proximal edge 64 of the standing up section of the leg cuffs 34.

The barrier leg cuffs 34 may be integral with the topsheet 24 or the backsheet 25 or may be a separate material joined to the absorbent article's chassis. The material of the barrier leg cuffs 34 may extend through the whole length of the diapers but may be "tack bonded" to the topsheet 24 towards the front waist edge 10 and rear waist edge 12 of the absorbent article so that in these sections the barrier leg cuff material remains flush with the topsheet 24.

Each barrier leg cuff 34 may comprise one, two or more elastic strands or strips of film 35 close to this free terminal edge 66 to provide a better seal.

In addition to the barrier leg cuffs 34, the absorbent article may comprise gasketing cuffs 32, which are joined to the chassis of the absorbent article, in particular to the topsheet 24 and/or the backsheet 25 and are placed externally relative to the barrier leg cuffs 34. The gasketing cuffs 32 may provide a better seal around the thighs of the wearer. Each gasketing leg cuff may comprise one or more elastic strings or elastic elements in the chassis of the absorbent article between the topsheet 24 and backsheet 25 in the area of the leg openings. All or a portion of the barrier leg and/or gasketing cuffs may be treated with a lotion or skin care composition. The barrier leg cuffs may be constructed in a number of different configurations, including those described in U.S. Pat. App. Publ. No. 2012/0277713.

Front and Rear Ears

In a form, the absorbent article may comprise front ears 46 and rear ears 40. The ears may be an integral part of the chassis, such as formed from the topsheet 24 and/or backsheet 25 as side panel. Alternatively, as represented on FIG. 1, the ears (46, 40) may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Liquid Management System (LMS)

One function of the LMS 50 is to quickly acquire the fluid and distribute it to the absorbent core 28 in an efficient manner. The LMS 50 may comprise one or more layers, which may form a unitary layer or may remain as discrete layers which may be attached to each other. The LMS 50 may comprise two layers: a distribution layer 54 and an acquisition layer 52 disposed between the absorbent core and the topsheet, but the present disclosure is not limited to such a configuration.

The LMS 50 may comprise SAP as this may slow the acquisition and distribution of the fluid. In other forms, the LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example.

Distribution Layer

The LMS 50 may comprise a distribution layer 54. The distribution layer 54 may comprise at least 50% or more by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf).

Figure 9:
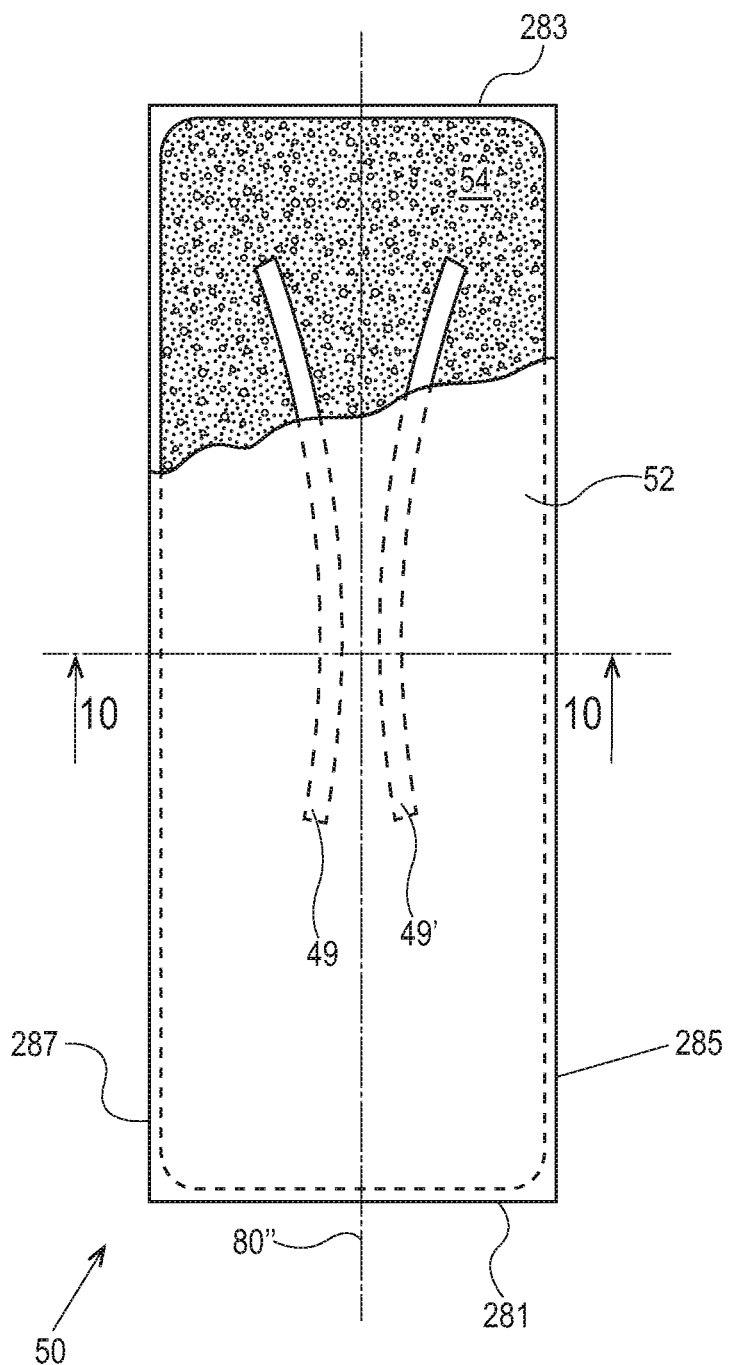
FIG. 9 is a top view of a LMS of the absorbent article of FIG. 4 with some layers partially removed in accordance with the present disclosure.
Figure 10:
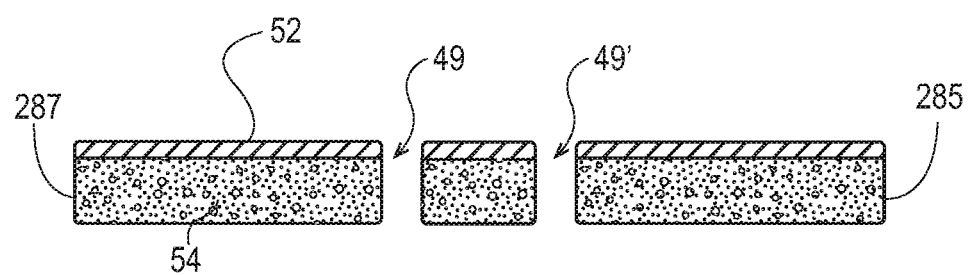
FIG. 10 is a cross-sectional view of the liquid management system taken about line 10-10 of FIG. 9 in accordance with the present disclosure.

The example LMS 50 of the absorbent article of FIGS. 4-5 is shown in isolation in FIGS. 9-10 where FIG. 10 is a cross-sectional view of the LMS 50 taken about line 10-10 of FIG. 9. The LMS 50 may comprises a front side 281, a rear side 283, and two longitudinal sides 285, 287 joining the front side 281 and the rear side 283. The LMS 50 may also comprise a generally planar top side with a surface area and a generally planar bottom side with a surface area. The front side 281 of the LMS is the side of the LMS intended to be placed towards the front waist edge 10 of the absorbent article. The LMS 50 may have a longitudinal axis 80" corresponding substantially to the longitudinal axis 80 of the absorbent article, as seen from the top in a planar view as in FIG. 1. In the illustrated form, the LMS 50 comprises a distribution layer 54 and an acquisition layer 52 which cooperate to define the channels 49, 49'. In other forms, less than all of the layers of the LMS 50 may define the channel such that at least one layer of the LMS 50 is continuous while another layer of the LMS 50 is discontinuous.

Acquisition Layer

The LMS 50 may alternatively or additionally comprise an acquisition layer 52. The acquisition layer 52 may be disposed, for example, between the distribution layer 54 and the topsheet 24. The acquisition layer 52 may be or may comprise a non-woven material, such as an SMS or SMMS material, comprising a spunbonded, a melt-blown and a further spunbonded layer or alternatively a carded chemical-bonded nonwoven. The acquisition layer 52 may comprise air or wet-laid cellulosic, cross-linked cellulosic, or synthetic fibers, or blends thereof. The acquisition layer 52 may comprise a roll-stock web of synthetic fibers (which may be processed to increase void space, such as by solid state formation), or a combination of synthetic and cellulosic fibers, bonded together to form a highloft material. Alternatively, the acquisition layer 52 may comprise absorbent open cell foam. The nonwoven material may be latex bonded.

Channels in Liquid Management System

The LMS 50 of the absorbent article 20 may comprise channels that may generally enable better conformation of the absorbent article to the wearer's anatomy, leading to increased freedom-of-movement and reduced gapping. One or more of the channels of the LMS 50 may be configured to work in concert with various channels in the absorbent core 28, as discussed above. Furthermore, channels in the LMS 50 may also provide increased void space to hold and distribute urine, BM or other bodily exudates within the absorbent article, leading to reduced leakage and skin contact. Channels in the LMS 50 may also provide internal serviceable indicia, especially when highlighted via physical differences in texture, color, and/or pattern, to facilitate achieving the correct alignment of the absorbent article on a wearer. Thus, such physical differences may be, for example, visually and/or tactilely noticeable.

Similar to the channels in the absorbent core 28, a channel in the LMS 50 may be any region in a layer, or extending through more than one layer, that has a substantially lower basis weight or thickness than the surrounding material, as set forth in the definition of "channel" above. The channels in the LMS 50 may also serve to reduce the tension forces to enable controlled bending and maintain the LMS 50 in close proximity to the absorbent core 28. Thus, the presence of channels in the LMS 50, which may or may not be aligned with any channels in an underlying absorbent core 28, may generally function as hinges to allow for a more flexible composite structure. In some cases, for example, the channels of the LMS 50 allow for the LMS 50 to move toward the absorbent core 28 in a controlled bending arrangement, thereby limiting the separation between the LMS 50 and the absorbent core 28. Moreover, a channel in the LMS 50 may assist in the routing of fluid or other bodily exudates from one region of the absorbent article 20 to another region of the absorbent article 20. Such routing may desirably improve the overall distribution of fluid through the absorbent article 20 and may lead to increase in comfort, wearability, or longevity of the article.

For multi-layered LMSs, the channels may be present in one or more layers of the LMS 50 and may vary in their dimensions in all three planes of reference. The width of a given channel in the LMS 50 may vary in the longitudinal direction (i.e., in a direction substantially parallel to the longitudinal axis of the absorbent article). A channel may also have a different width, length, and/or volume in front of a lateral axis or lateral separation element of the absorbent article than behind the lateral axis or lateral separation element. The channels of the LMS 50 may have a range of widths, lengths, shapes, volumes, and patterns, similar to the channels described above with regard to the absorbent core 28.

One or more channels in the LMS 50 may at least partially overlap, or fully overlap, a channel in the absorbent core 28, creating a deeper recess in the overlapping regions. For forms where the LMS 50 includes more than one layer, the layer closest to the absorbent core 28 may include a channel. One or more layers in the structure, such as the topsheet 24, an acquisition layer 52, distribution layer 54, or other layers, may be bonded to an element of the absorbent core 28 in this region to increase the depth of the combined channel. In a form, the channel in the acquisition layer 52 of the LMS 50 and the channel in the absorbent core 28 are coincident such that the channels are completely overlapping. In another form, channels in the LMS and storage layers have no overlapping area. Other forms have a vertical overlap between the channels in the two layers that encompass the intervening range such that they partially overlap.

Referring again to FIGS. 1-5, the LMS 50 in the illustrated example is shown defining two channels 49, 49'. The channels 49, 49' are at least partially oriented in the longitudinal direction of the absorbent article 80 (i.e., has a longitudinal vector component). Other channels in the LMS may be at least partially oriented in the lateral direction (i.e., has a lateral vector component), or in any other direction, and the channels in the LMS 50 may be continuous or intermittent. Some channels in the LMS may be round, oblong, square, rectangular, triangular or any other suitable shape. The channels may be formed in various ways. For example, the channels may be formed by zones within the LMS 50 which may be substantially free of, or free of, acquisition or distribution material.

The channels of the LMS 50 may be present at least at the same longitudinal level as the lateral axis 90 in the absorbent article, as represented in FIG. 1 with the two longitudinally extending channels 49, 49'. The channels may also extend from the crotch region 7 or may be present in the front waist region 5 and/or in the rear waist region 6 of the absorbent article. In FIG. 1, the channels 49, 49' are generally coincident with channels 26, 26', with channels 26, 26' having a longer length in the longitudinal direction towards the front waist edge 10 of the absorbent article 20.

The LMS 50 may define any suitable number of channels, such as at least one or more than two channels. Shorter channels may also be present, for example in the rear waist region 6 or the front waist region 5 of the LMS 50. The channels of the LMS 50 may comprise one or more pairs of channels symmetrically arranged, or otherwise arranged relative to the longitudinal axis 80 and/or the lateral axis 90, or other transverse axis. The channels may extend substantially longitudinally or substantially laterally.

At least some or all of the channels in the LMS 50 may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the topsheet 24 to the backsheet 25 together through a channel of the LMS 50. Typically, an adhesive may be used to bond the topsheet 24 and the backsheet 25 through the channels, but it is possible to bond via other known processes, such as pressure bonding, ultrasonic bonding, heat bonding, or combination thereof. The topsheet 24 and the backsheet 25 may be continuously bonded or intermittently bonded along or within portions of or all of the channels.

In a form, referring to FIG. 1, the LMS 50 may comprise at least two channels (e.g., 49, 49'). These channels may be free of, or substantially free of (e.g., less than 10%, less than 5%, less than 3%, less than 2%, or less than 1%), non-woven material or cross-linked cellulose fibers and may be at least partially oriented in the longitudinal direction and/or may be at least partially oriented in the lateral direction.

While portions of the channels 26, 26' of the absorbent core 28 and the channels 49, 49' of the LMS 50 shown in FIGS. 1-10 are generally aligned, this disclosure is not so limited. In fact, as is to be appreciated, particular arrangements of the channels in an LMS 50 and/or an absorbent core 28 may vary.

Pants

An alternate configuration for absorbent articles is one for absorbent pants in which the central chassis structure does not extend to, or form, the front and rear waist edges of the pant. Rather, an elasticized belt structure entirely encircles the wearer's waist and forms the waist edge about the entire pant, and the side/hip panels. The central chassis is joined to the belt structure, usually on the inside thereof, with its ends disposed at locations in the front and rear waist regions somewhat below the waist edges of the belt structure. The elastic belt is usually relatively wide (in the longitudinal direction) and elastically stretchable in the lateral direction. It entirely encircles the wearer's waist, and thereby covers a relatively large amount of the wearer's skin. This configuration is sometimes known as a "belt" or "balloon" configuration (hereinafter, "belt" configuration).

In more detail, an absorbent article may have a front region, a rear region, and a crotch region disposed therebetween, further comprising a liquid permeable topsheet, a backsheet, and an absorbent core disposed between the topsheet and the backsheet. The article then may have a central chassis occupying the crotch region, and a belt structure disposed about the central chassis, the belt structure overlaying the backsheet to the outside thereof in the front and rear regions, and the belt structure overlapping and extending laterally and longitudinally outward from the chassis. The belt structure may comprise an outer nonwoven and an inner nonwoven and have elastic strands therebetween. The belt structure may further have a front belt portion having a front waist edge, and front left and right side edges; and a rear belt portion having a rear waist edge and rear left and right side edges, wherein the respective front and rear left side edges and the respective front and rear right side edges are joined, forming a waist opening and left and right leg openings.

Any pant configuration may have any of the article components described herein, for example, the topsheet, backsheet, core, barrier cuffs, and/or liquid management system layers described herein, along with the odor control composition and its placement. Further descriptions and embodiments of pant configurations may be found in U.S. Ser. No. 62/210,635.

Placement of Odor Control Composition

The placement of the odor control composition of the present invention can allow it to be concealed from view from outside the article. This is particularly advantageous if the odor control composition is a dark color, for example, particles of activated carbon. As such, the odor control composition of the present invention may be placed between components of the article, wherein, depending on the opacity and/or thickness of the components, the odor control composition is not visible, yet may still be effective. For example, the odor control composition may be disposed between the core wrap and the liquid management system. For example, the odor control composition may be disposed between the distribution layer and the core wrap. In some cases, the odor control composition may be disposed between an acquisition layer and the core wrap, between an acquisition layer and the distribution layer, between two acquisition layers, or between an acquisition layer and the topsheet. One advantage of placement within or between the liquid management system and the core wrap, in addition to the lack of visibility, is that such placement may limit interaction with glues and/or core materials and in general, limit the odor control composition's interaction with the functions of other components. In many cases, it may be desired that the odor control composition be not visible when an open article is viewed from the top (an observer looking at the topsheet side of the article in ordinary light) or when viewed from the backsheet side of the article in ordinary light. In some cases, the odor control composition may be placed in a location such that the odor control composition is blocked from viewed. The odor control composition in general may be disposed such that at least two or three layers of article components are disposed above it towards the topsheet of the article. There may be one, two, or three layers between the odor control composition and the topsheet.

In some embodiments, the odor control composition may be activated carbon and may be deposited directly into the core, for example, inside the core wrap or mixed into the SAP. This particularly secures the odor control composition in place, as it is enclosed and secured inside the core wrap. It also provides security that the activated carbon is not visible when the article is viewed from the outside, ie., from either the topsheet side or the backsheet side.

In general, many of the article components as described herein may be planar, having a surface and a surface area on each side, one surface oriented towards the topsheet side of the article, and the other surface oriented towards the backsheet side of the article. Such article components may include, for example, the topsheet, acquisition layer(s), distribution layer(s), liquid management system, backsheet, core, or core wrap. In the case of the core wrap, the core wrap may have a surface that is the outermost surface oriented towards the topsheet, and the core wrap may also have a surface that is the outermost surface oriented towards the backsheet, while also having interior surfaces oriented towards the absorbent core. The core wrap surface area may be oriented towards the topsheet and be adjacent to the liquid management system.

In some cases, adjacent article components may have similar or substantially similar surface areas, but in some cases, adjacent article components may not have similar or substantially similar surface areas. For example, in some cases, the distribution layer surface area may be less than the adjacent core wrap surface area. In some cases, any acquisition layer surface area or distribution layer surface area may be about 40%, 50%, 60%, 70%, 80%, or 90% of the size of the core wrap surface area oriented towards the topsheet. In some cases, the length of any acquisition layer or distribution layer may be about 40%, 50%, 60%, 70%, 80%, or 90% of the length of a core wrap surface.

In some cases, the odor control composition may be placed over at most about 25%, 30%, 35%, 40%, 45%, 50%, 55%, 60%, 65%, 70%, 75%, 80%, 85%, 90%, 95%, or 100% of a surface area. In some cases, the odor control composition may be placed on at most about 80% of the core wrap surface area. In some cases, however, the odor control composition may be placed on only about 1% to about 5% of the core wrap surface area, from about 1% to about 10%, from about 1% to about 20%, from about 2% to about 10%, from about 5% to about 10%, from about 5% to about 15%, or from about 5% to about 20% of the core wrap surface area.

The odor control composition may be placed on the part of the surface area of a component that overlaps with the adjacent component's surface area. For example, a particulate activated carbon may be sprinkled on about 50% of the core wrap surface area that is oriented towards the topsheet. The adjacent article component may be the distribution layer, which may have a smaller surface area than the core wrap. Therefore, the particulate activated carbon may be sprinkled only on the surface area of the core wrap that touches the distribution layer surface area. In any event, by placing the odor control composition underneath several layers, or at least underneath sufficiently opaque component layers, the odor control composition will not be visible from the topsheet side of the article. An adhesive may be used to help keep the odor control composition in place, or an adhesive may not be used in some embodiments.

The odor control composition may be disposed on an article component in any way that allows the composition to function as an odor control composition. Suitable forms may include, but are not limited to, a particulate, a powder, a fiber, a paper, a nonwoven, or a slurry. In some cases, the odor control composition may be comprised in additional materials, such as a carrier, a coating, or an ink. The odor control composition may be incorporated directly into a fiber or nonwoven substrate component of the article. The odor control composition may be contained inside a pouch or sachet, or may be in the form of a laminate or film.

In one particular embodiment, an absorbent article comprises a topsheet and a backsheet with an absorbent core between, the core comprising a core wrap. The article comprises a liquid management system comprising an acquisition layer and a distribution layer, wherein the distribution layer is adjacent to the core wrap surface oriented toward the topsheet. An odor control composition, particulate activated carbon, is placed on top of the core wrap surface oriented toward the topsheet. The activated carbon covers approximately 2 cm$^2$ of the core wrap surface, placed in two piles, each 1 cm$^2$ in area. The length of the distribution layer is about 50% the length of the adjacent core wrap, and the particulate activated carbon is placed on the core wrap only where the core wrap is overlapped by the distribution layer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A disposable absorbent article comprising a longitudinal centerline and a lateral centerline, a front waist region with a front waist edge, a rear waist region with a rear waist edge, a crotch region disposed between the front and rear waist regions, and two spaced apart longitudinal side edges joining the front waist edge to the rear waist edge, comprising:
   a) a topsheet;
   b) a backsheet;
   c) an absorbent core disposed between the topsheet and the backsheet, the absorbent core comprising a core wrap; and
   d) a liquid management system disposed between the topsheet and the absorbent core, the liquid management system comprising a distribution layer, wherein the distribution layer comprises a distribution layer surface area that faces the core wrap;
   wherein an odor control composition is directly joined to a core wrap surface area facing the liquid management system;
   wherein the core wrap surface area facing the liquid management system comprises a continuous surface free of apertures;
   wherein the distribution layer surface area is less than the core wrap surface area; and
   wherein the odor control composition is disposed only on a portion of the core wrap surface area that is overlapped by the distribution layer.

2. The article of claim 1, wherein the odor control composition comprises activated carbon, zeolites, silica, or combinations thereof.

3. The article of claim 1, wherein the odor control composition is a particulate, a powder, a pouch, a laminate, a film, a fiber, a paper, a nonwoven, a substrate, or a slurry.

4. The article of claim 1, wherein the odor control composition does not comprise a coating, a carrier, or an ink.

5. The article of claim 1, wherein the liquid management system comprises an acquisition layer and a distribution layer.

6. The article of claim 5, wherein the acquisition layer is disposed between the topsheet and the distribution layer.

7. The article of claim 1, wherein the odor control composition is not visible when the article is viewed from a topsheet side of the article.

8. The article of claim 1, wherein the odor control composition is placed over at least 50% of the core wrap surface area.

9. The article of claim 1, wherein the odor control composition is placed over about 1% to about 5% of the core wrap surface area.

10. The article of claim 1, wherein the odor control composition is incorporated directly into the core wrap surface area.

11. The article of claim 1, wherein the liquid management system comprises a distribution layer; and wherein a length of the distribution layer is from about 40% to about 80% of a length of the core wrap.

12. The article of claim 1, wherein the article comprises:
    a) a fastening system for joining the front waist region to the rear waist region when the absorbent article is configured as worn;
    b) barrier cuffs disposed adjacent to and inboard of the longitudinal side edges;
    c) gasketing cuffs disposed between the longitudinal side edges and the barrier cuffs;
    d) front ears disposed in the front waist region;
    e) back ears disposed in the rear waist region; or
    f) at least one hot melt adhesive composition suitable for joining at least two absorbent article components together.

13. The article of claim 1, wherein the absorbent core comprises less than about 2% by weight of absorbent material contained within the core wrap of cellulose.

14. A disposable absorbent article comprising a longitudinal centerline and a lateral centerline, a front waist region with a front waist edge, a rear waist region with a rear waist edge, a crotch region disposed between the front and rear waist regions, two spaced apart longitudinal side edges joining the front waist edge to the rear waist edge, and comprising:
    a) a topsheet;
    b) a backsheet;
    c) an absorbent core disposed between the topsheet and the backsheet, wherein the absorbent core comprises a nonwoven core wrap, and wherein the absorbent core comprises less than about 2% by weight of absorbent material contained within the core wrap of cellulose; and
    d) a liquid management system disposed between the topsheet and the absorbent core, the liquid management system comprising a distribution layer, wherein the distribution layer comprises a distribution layer surface area that faces the core wrap;
    wherein activated carbon, zeolite, and/or silica are directly joined to a topsheet-facing surface of the core wrap;
    wherein the topsheet-facing surface of the core wrap comprises a continuous surface free of apertures;
    wherein the distribution layer surface area is less than the core wrap surface area; and
    wherein the activated carbon, zeolite, and/or silica are disposed only on a portion of the core wrap surface area that is overlapped by the distribution layer.

15. The article of claim 14, wherein the activated carbon, zeolite, and/or silica is a particulate, a powder, a fiber, a paper, a nonwoven, a laminate, a film, or a slurry.

16. The article of claim 14, wherein the liquid management system comprises an acquisition layer and a distribution layer, wherein the acquisition layer is disposed between the topsheet and the distribution layer.

17. The article of claim 14, wherein the activated carbon, zeolite, and/or silica is not visible when the article is viewed from a topsheet side of the article.

18. The article of claim 14, wherein the activated carbon, zeolite, and/or silica is placed over about 1% to about 20% of the topsheet-facing surface of the core wrap.

19. The article of claim 14, wherein the article comprises:
a) a fastening system for joining the front waist region to the rear waist region when the absorbent article is configured as worn;
b) barrier cuffs disposed adjacent to and inboard of the longitudinal side edges;
c) gasketing cuffs disposed between the longitudinal side edges and the barrier cuffs;
d) front ears disposed in the front waist region;
e) back ears disposed in the rear waist region; or
f) at least one hot melt adhesive composition suitable for joining at least two absorbent article components together.

20. A disposable absorbent article comprising a longitudinal centerline and a lateral centerline, a front waist region with a front waist edge, a rear waist region with a rear waist edge, a crotch region disposed between the front and rear waist regions, two spaced apart longitudinal side edges joining the front waist edge to the rear waist edge, and comprising:
a) a topsheet;
b) a backsheet;
c) an absorbent core disposed between the topsheet and the backsheet, wherein the absorbent core comprises a nonwoven core wrap;
d) a liquid management system disposed between the topsheet and the absorbent core, the liquid management system comprising an acquisition layer and a distribution layer; and
e) an odor control composition comprising activated carbon, zeolites, silica, or combinations thereof;
wherein the odor control composition is disposed between the acquisition and distribution layers; and
wherein a topsheet-facing surface of the core wrap comprises a continuous surface free of apertures.

* * * * *